Sept. 16, 1958 W. FLEMER III Plant Pat. 1,752
HONEY LOCUST TREE
Filed Jan. 29, 1958
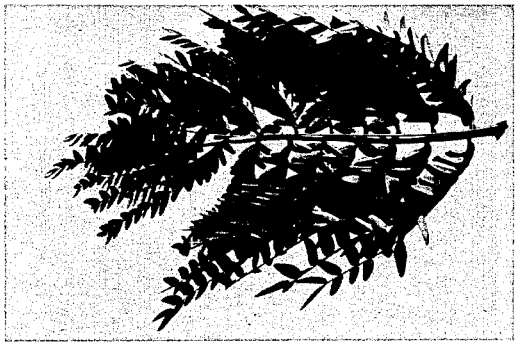
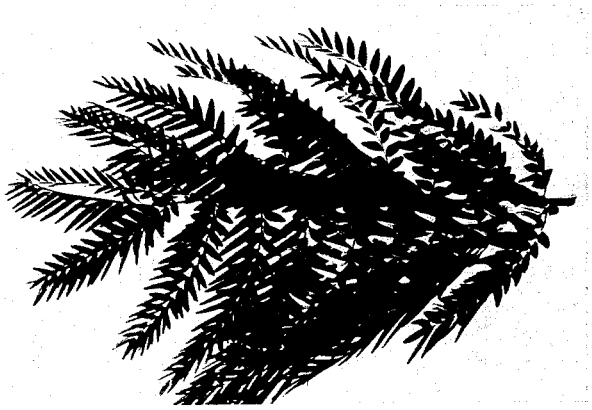
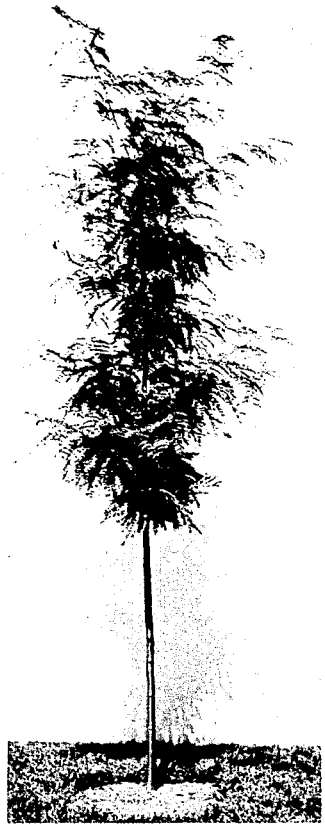
INVENTOR
William Flemer, III
BY Robert Robb
ATTORNEYS United States Patent Office Plant Pat. 1,752
Patented Sept. 16, 1958

1,752

HONEY LOCUST TREE

William Flemer III, Princeton, N. J., assignor to Princeton Nurserymen's Research Associates, Kingston, N. J., a partnership Application January 29, 1958, Serial No. 712,052

1 Claim. (Cl. 47—59)

The present invention relates to a new and distinct variety of thornless honey locust tree which was discovered by me as a newly found seedling of *Gleditsia triacanthus inermis* in a transplanted block of seedlings of the latter variety which were being grown in a cultivated area under my control, direction and supervision in Plainsboro Township, Plainboro, New Jersey.

At the time of my discovery, the new seedling was about 14 feet tall, and my attention was initially attracted thereto by its dark Green foliage (almost a dark Blue-Green in appearance), its huge, finely divided leaves which gave an effect of green lace, and its exceptionally sturdy trunk and branches, these features being unique and distinct as compared with common varieties then being grown by me, as well as in comparison with all other varieties of which I was aware.

Following my initial discovery, I promptly took steps to preserve and observe the new seedling, as well as to asexually reproduce the same by budding, as performed by me at Plainsboro, New Jersey. Prolonged observation confirmed the unique characteristics originally noticed, as referred to above, and established other new and distinct characteristics which, taken altogether, represent a new combination which may be briefly summarized as follows:

(1) An extremely symmetrical and upright habit of growth, with large, thick branches of a greater diameter and greater stiffness than any other honey locust, thereby making the tree unusually resistant to ice damage and to breakage during severe windstorms;

(2) An excurrent habit of growth, as characterized by a very strong and straight central leader which extends up through the crown of the tree, rather than dividing up into a number of equal and more or less parallel central branches which are subject to severe damage due to wind and sleet storms such as is characteristic of ordinary honey locust trees;

(3) A very smooth and glossy bark which has a "waxed" appearance;

(4) Slightly rippled or sinuous habit of the branches during the young stages of the tree, which disappear as the branches enlarge in diameter;

(5) Extremely large and very finely cut foliage, giving a fern-like effect by reason of the unusually large number of leaflets on each leaf, said foliage tending to droop slightly because of its exceptionally heavy texture; and (6) An unusually dark Green color of the foliage which may be described as almost a dark Blue-Green.

Although the parentage of my new seedling is not definitely known, I am convinced that it represents a new and improved variety which is distinguished from all other varieties and which make it an ideal type for lawn and yard planting.

The accompanying drawing shows a typical tree of my new variety, as well as typical specimens of the foliage thereof as the latter appears from both upper and lower surfaces on an enlarged scale, all as depicted in color as nearly true as it is reasonably possible to make the same in a color illustration of this character.

The following is a detailed description of my new variety, with color terms in accordance with the Munsell Book of Color, except where general color terms of ordinary dictionary significance are obvious:

Parentage: A newly found seedling of an unpatented variety of *Gleditsia triacanthus inermis.*

Propagation: Holds it distinguishing characteristics through succeeding propagations by budding (sometimes termed "bud-grafting").

Locality where grown and observed: Princeton, New Jersey.

Tree: Large; very strong-growing; upright; very dense; symmetrical; hardy; non-productive.

*Trunk.*—Stocky; smooth; slightly sinuate in young stages; maintains a central leader up through the crown of the tree. Bark—very smooth and glossy, giving an almost "waxed" appearance.

*Head.*—Obovate.

*Branches.*—Exceptionally stout and thick; stiff; slightly sinuate; ascending; smooth; excurrent habit; unusually resistant to ice and windstorm damage. Color—Dull Chestnut Brown.

*Lenticels.*—Moderately abundant; small.

Foliage:

*Leaves.*—Exceptionally large; leathery; bipinnate; from 21 to 23 pinnae per leaf, and from 32 to 34 leaflets per pinna; average length from 35 to 42 cm.; average width from 35 to 40 cm. Color.—upper surface—Dark Forest Green, Plate 2.5 G 3/4; under surface—Medium Emerald Green, Plate 5.0 GY 6/6.

*Leaflets.*—Unequally cuneate-lanceolate; from 2.6 to 2.9 cm. in length; from 10 to 12 mm. in width.

*Rachis.*—Sparingly pubescent; deeply grooved.

*Margin.*—Serrulate.

*Petiole.*—Long; thick.

*Glands.*—None.

*Stipules.*—Produced only on earliest leaves in growing season; from 2¼ to 2½ cm. long.

Flower buds: Depressed; inconspicuous; small; subglobose; minutely pubescent.

Flowers: Late, as compared with other varieties; small; few; only staminate flowers produced.

*Color.*—Pale Green-Yellow, Plate 2.5 GY 8/6.

Fruit: None produced to date.

Disease and insect resistance: The foliage is more resistant to Mimosa web worm damage than that of any other variety, and is especially resistant to spider mite damage, as compared with other varieties grown under comparable cultural conditions at Princeton, New Jersey.

I claim:

A new and distinct variety of thornless honey locust tree, substantially as herein shown and described, characterized particularly as to novelty by the unique combination of an extremely symmetrical and upright habit of growth, large, thick and stiff branches which are unusually resistant to ice and windstorm damage, an excurrent habit of growth as evidenced by a very strong and straight central leader which extends up through the crown of the tree, a very smooth and glossy bark which has a "waxed" appearance, a slightly rippled or sinuous form of the branches during the young stages of the tree which disappears as the branches enlarge in diameter, extremely large and very finely cut foliage of heavy texture and an unusually large number of leaflets on each leaf which give a fern-like effect, said foliage tending to droop slightly, and the exceptionally dark Green color of the foliage.

No references cited.